(12) United States Patent
Tang et al.

(10) Patent No.: US 9,926,286 B2
(45) Date of Patent: Mar. 27, 2018

(54) VORTIOXETINE INTERMEDIATE AND SYNTHESIS PROCESS THEREOF

(71) Applicants: SHANGHAI SYNCORES TECHNOLOGIES INC. LTD., Shanghai (CN); ZHEJIANG HUAHAI PHARMACEUTICAL CO., LTD, Taizhou, Zhejiang (CN)

(72) Inventors: Caide Tang, Shanghai (CN); Gang Wang, Shanghai (CN); Boyu Wang, Shanghai (CN); Luning Huang, Shanghai (CN); Eric Gu, Shanghai (CN)

(73) Assignees: SHANGHAI SYNCORES TECHNOLOGIES INC. LTD., Shanghai (CN); ZHEJIANG HUAHAI PHARMACEUTICAL CO., LTD, Zhejiang (CN)

( * ) Notice: Subject to any disclaimer, the term of this patent is extended or adjusted under 35 U.S.C. 154(b) by 0 days.

(21) Appl. No.: 15/126,890

(22) PCT Filed: Mar. 25, 2015

(86) PCT No.: PCT/CN2015/075018
§ 371 (c)(1),
(2) Date: Sep. 16, 2016

(87) PCT Pub. No.: WO2015/169130
PCT Pub. Date: Nov. 12, 2015

(65) Prior Publication Data
US 2017/0088530 A1    Mar. 30, 2017

(30) Foreign Application Priority Data
May 9, 2014    (CN) .......................... 2014 1 0193538

(51) Int. Cl.
*C07D 295/096*    (2006.01)
*C07D 295/185*    (2006.01)

(52) U.S. Cl.
CPC ..... *C07D 295/096* (2013.01); *C07D 295/185* (2013.01)

(58) Field of Classification Search
CPC ................................................ C07D 295/096
See application file for complete search history.

(56) References Cited

U.S. PATENT DOCUMENTS 6,277,852 B1 * 8/2001 Howard ............... C07D 207/34
514/252.13

FOREIGN PATENT DOCUMENTS

EP         548798    *  6/1993
WO    WO 2013051672    *  4/2011

OTHER PUBLICATIONS

Koga et al. (Journal of Medicinal Chemistry (1980), 23(12), 1358-63).*

* cited by examiner

*Primary Examiner* — Bruck Kifle
(74) *Attorney, Agent, or Firm* — Norton Rose Fulbright US LLP

(57) ABSTRACT

The present invention provides a new intermediate II and a method for synthesizing the same. The method comprises: (a) firstly diazotizing a compound of formula I as a raw material, and then halogenating to obtain an intermediate II; and (b) reacting the intermediate II with a compound III to obtain a compound IV, hydrolyzing the obtained compound IV directly without being separated to obtain Vortioxetine represented by compound V. The intermediate II can be used for synthesizing Vortioxetine.

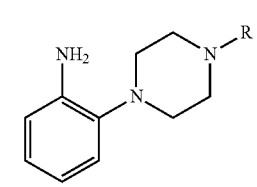

I

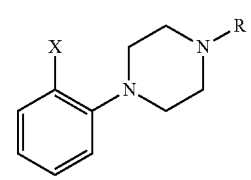

II

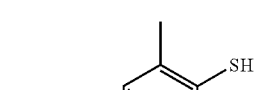

III

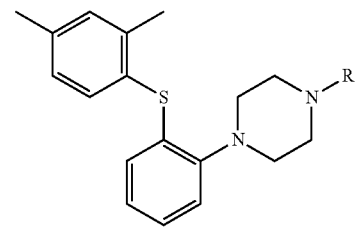

IV

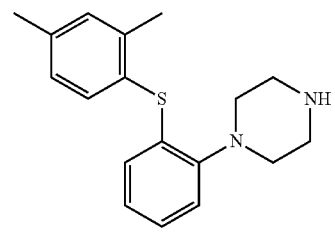

V

19 Claims, No Drawings

VORTIOXETINE INTERMEDIATE AND SYNTHESIS PROCESS THEREOF

CROSS-REFERENCE TO RELATED APPLICATIONS

The present application is a national phase application under 35 U.S.C. § 371 of International Application No. PCT/CN2015/075018 filed Mar. 25, 2015, which claims priority to Chinese patent application of No. 201410193538.9, filed May 9, 2014. The entire contents of the referenced applications are incorporated into the present application by reference.

FIELD OF INVENTION

The present invention belongs to the field of pharmaceutical chemical industry, and in particular relates to a new compound intermediate applicable to preparing Vortioxetine as an antidepressant, a method for synthesizing Vortioxetine intermediate and a new method for synthesizing Vortioxetine.

BACKGROUND OF THE INVENTION

Vortioxetine hydrobromide is a new medicine used for treating adult patients who have major depressive disorder, and developed by Lundbeck pharmaceutical company, the second biggest pharmaceutical manufacturer in Denmark. It is approved by U.S. Food and Drug Administration on Sep. 30, 2013. It has a chemical name of 1-[2-(2,4-dimethylphenylthio)phenyl]piperazine hydrobromide, and a following chemical structure:

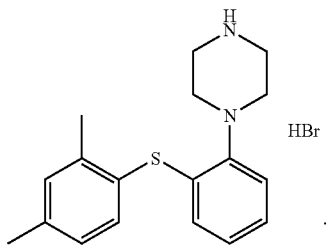 [SMILES: Cc1ccc(Sc2ccccc2N2CCNCC2)c(C)c1 ; Br]

Several synthesis routes of Vortioxetine and the derivatives thereof are disclosed in the PCT Publication WO2003029232.

Synthesis route I is shown as follows:

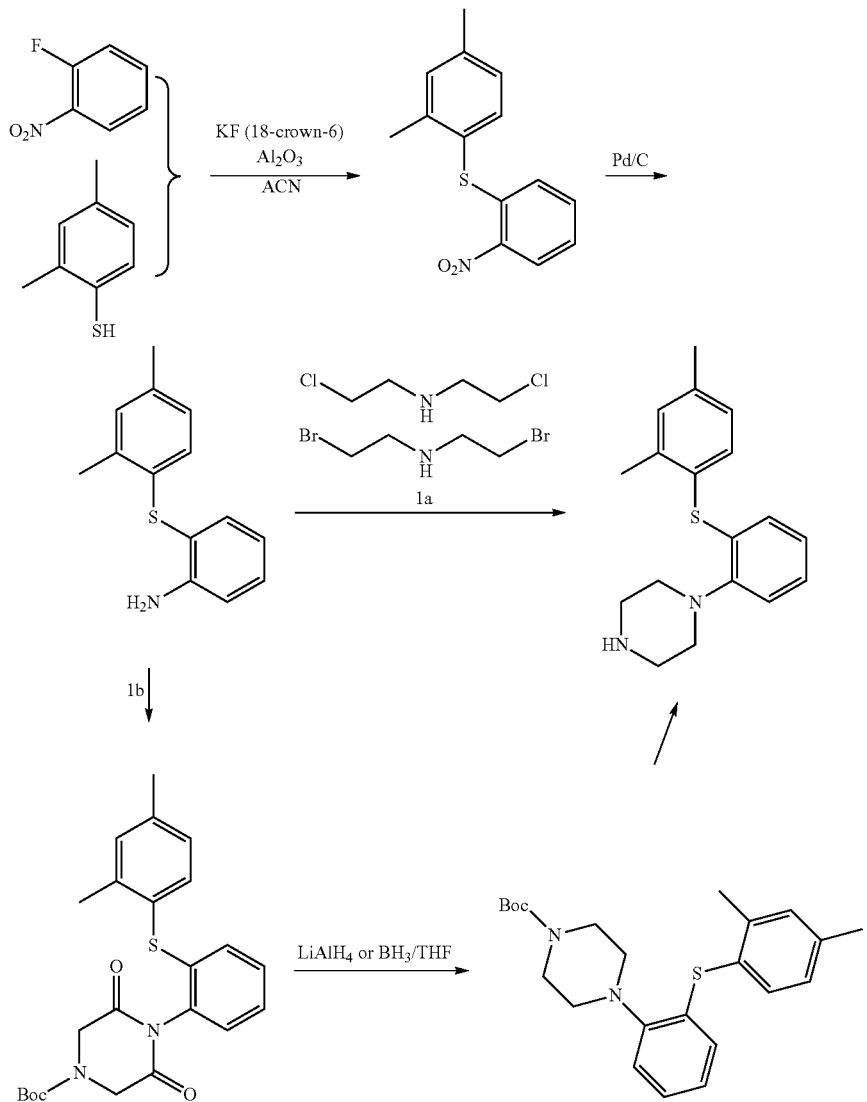

Ortho-fluoronitrobenzene and 2,4-dimethyl thiophenol are used as raw materials to synthesize an intermediate (2,4-dimethylphenyl)(2-nitrophenyl)thioether. Then an intermediate (2,4-dimethylphenyl)(2-aminophenyl)thioether is obtained by catalytic hydrogenating with palladium/carbon. In route 1a, this intermediate is reacted with a mixture of di(2-bromoethyl)amine and di(2-chloroethyl)amine to obtain the final product Vortioxetine. In route 1b, the intermediate (2,4-dimethylphenyl)(2-aminophenyl)thioether is reacted with N-(tert-butoxycarbonyl) iminodiacetic acid to obtain an intermediate 1-tert-butoxycarbonyl-4-[(2,4-dimethylphenylthio)phenyl]-3,5-dioxopiperazine. It is reduced by lithium aluminum hydride or borane to obtain an intermediate 4-tert-butoxycarbonyl-[(2,4-dimethylphenylthio)phenyl]-1-piperazine, which is treated with hydrochloric acid to obtain the final product Vortioxetine.

The synthesis route 2 is shown as follows:

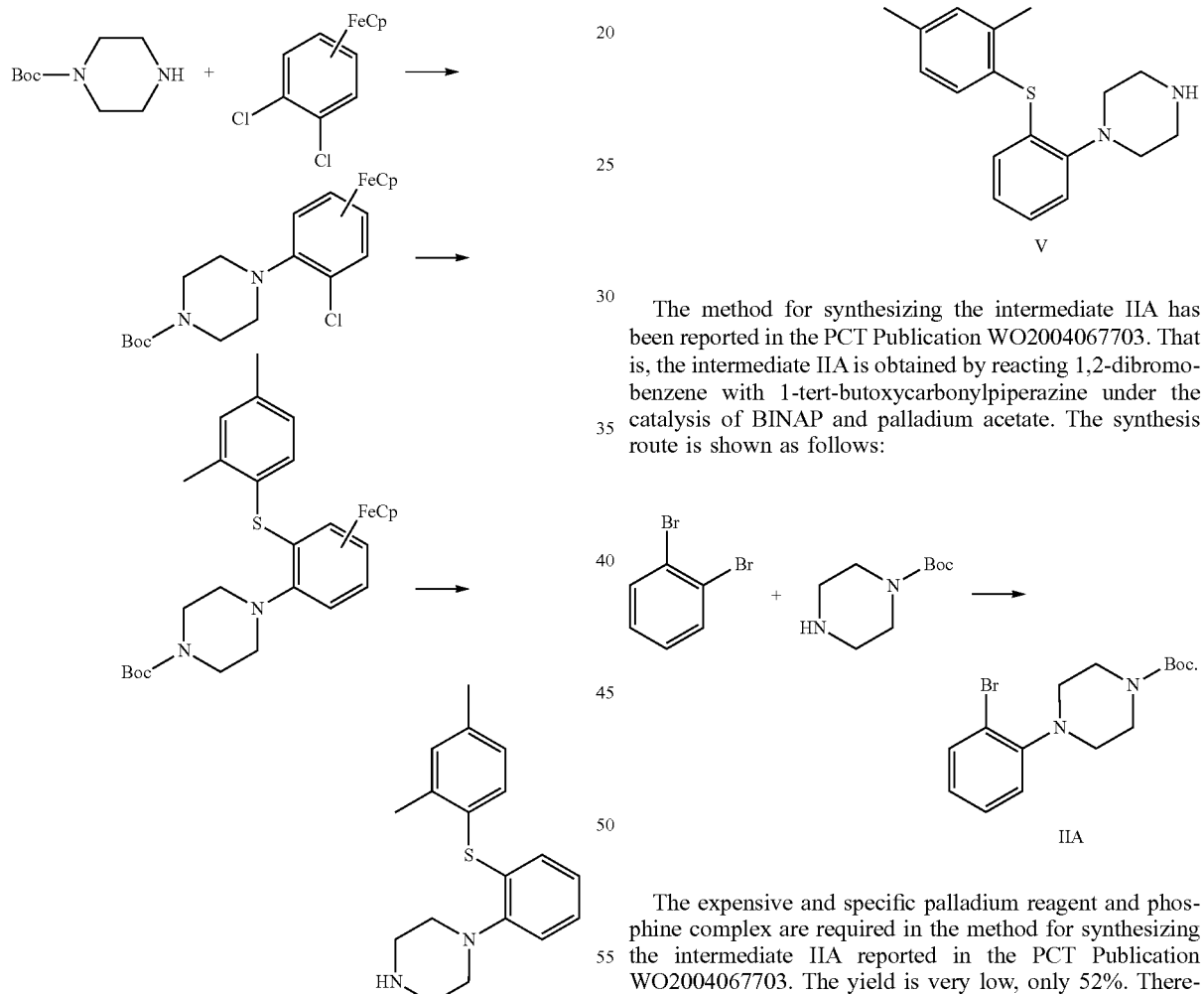

4-tert-butoxycarbonyl-1-piperazine as a raw material is reacted with η6-1,2-dichlorobenzene-η5-cyclopentadienyl iron(II) to obtain 4-({4-[η6-(2-chlorophenyl)η5-cyclopentadienyl iron(II)]-1-tert-butoxycarbonylpiperazine, which is then reacted with 2,4-dimethylthiophenol to obtain an intermediate. The final product Vortioxetine is then obtained by treating the obtained intermediate with hydrochloric acid.

Another synthesis route is disclosed in Journal of Medicinal Chemistry 2011, 54, 3206-3221:

The method for synthesizing the intermediate IIA has been reported in the PCT Publication WO2004067703. That is, the intermediate IIA is obtained by reacting 1,2-dibromobenzene with 1-tert-butoxycarbonylpiperazine under the catalysis of BINAP and palladium acetate. The synthesis route is shown as follows:

The expensive and specific palladium reagent and phosphine complex are required in the method for synthesizing the intermediate IIA reported in the PCT Publication WO2004067703. The yield is very low, only 52%. Therefore, the method is hard to industrialize, and the cost is very high.

Moreover, according to the prior art, during the process of preparing Vortioxetine, the compound IV is formed by reacting the intermediate IIA with the compound III, then separated, purified and further hydrolyzed to obtain Vortioxetine represented by compound V. However, it should be noted that by adopting this method to prepare Vortioxetine, the yield is not high and an additional separation step is involved, which increases the cost. It is not suitable for industrial production.

SUMMARY OF THE INVENTION

In a first aspect, the present invention provides a method for synthesizing an intermediate II:
in the compound of formula II:

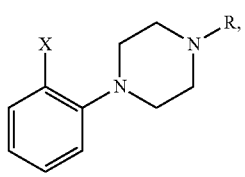

R is a protective group for amino, which can be selected from: tert-butoxycarbonyl (Boc), 9-fluorenylmethoxycarbonyl (Fmoc), carboxybenzyl (Cbz), acetyl (Ac) or trifluoroacetyl (Tfa); and R is preferably tert-butoxycarbonyl or acetyl;

X is halogen, selected from chlorine, bromine or iodine, and more preferably bromine, the method comprises the following steps:

firstly diazotizing the compound of formula I as a raw material, and then halogenating to obtain an intermediate II:

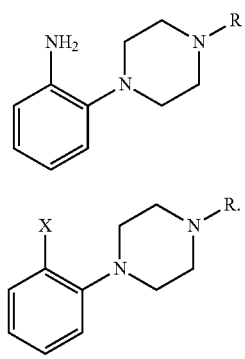

The synthesis of the compound of formula I as a raw material can refer to the example 1 of the present invention or other prior arts such as that described in Journal of Medicinal Chemistry, 2004, 47(3), 744-755, which is incorporated herein by reference in its entirety.

There are two methods for the diazotizing reaction of the compound of formula I, using $NaNO_2$/inorganic acid in water-oil system, and using alkyl nitrite (e.g., tert-butyl nitrite) in non-aqueous system. The said inorganic acid is HX or sulfuric acid.

The diazonium salt obtained from the diazotizing reaction is halogenated directly to obtain the corresponding compound II without being separated.

The halogenating agent used in halogenating reaction is selected from: NaX, KX, LiX, $MgX_2$, CuX, $CuX_2$ or a mixture of any two thereof or a mixture of copper sulfate and NaX, wherein the preferred halogenating agent is a mixture of CuBr and the aforementioned metal bromide, more preferably a mixture of cuprous bromide and sodium bromide, or a mixture of cuprous bromide and lithium bromide. The inventors found that the yield of compound II can be increased in particular by adopting the mixture of cuprous bromide and sodium bromide, or the mixture of cuprous bromide and lithium bromide as the halogenating agent.

The molar ratio of compound of formula I to halogenating agent is such that the compound of formula I is fully halogenated. It is preferably 1:1.5 to 1:8.0, more preferably 1:4, and still preferably 1:2. The inventors found that the yield of compound II can be increased by adopting the molar ratio of compound of formula I to the halogenating agent of 1:4. The temperature of the halogenating reaction is 20 to 100° C., preferably 65 to 85° C., and more preferably 75 to 85° C. The temperature of halogenating reaction of 65 to 85° C. is advantageous for the reaction system.

According to the method for preparing intermediate II of Vortioxetine provided in the present invention, the yield is relatively high, the use of expensive and specific palladium reagent and phosphine complex is avoided, and thus the cost of Vortioxetine is effectively reduced, thereby being suitable for industrial production. Moreover, the method for preparing the intermediate II of Vortioxetine of the present invention avoids the use of expensive and specific palladium reagent and phosphine complex, thus it also avoids the extreme process conditions related to the use of palladium reagent and phosphine complex, and is process-friendly.

In a second aspect, the invention provides a method for preparing Vortioxetine by one-pot reaction from intermediate II, comprising reacting the intermediate II with a compound III to obtain a compound IV, hydrolyzing the compound IV directly without being separated to obtain Vortioxetine represented by a compound V. The synthesis route is shown as follows:

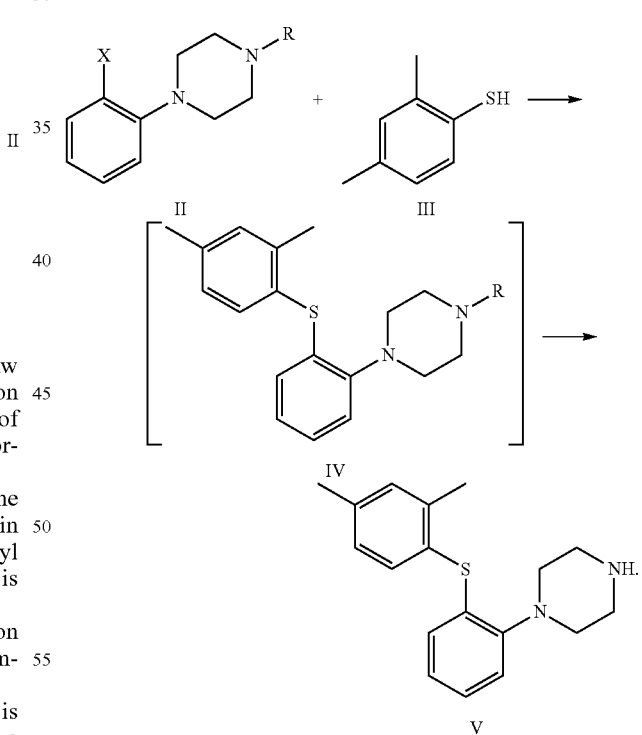

The inventors unexpectedly found that Vortioxetine can be obtained by directly hydrolyzing the compound IV obtained from reacting the intermediate II with the compound III without being separated. This can not only reduce the steps of synthesizing Vortioxetine thereby reducing the cost, but also increase the yield significantly. Moreover, the inventors apply the intermediate II of Vortioxetine prepared by the method for synthesizing Vortioxetine intermediate according to the first aspect of the invention into the method for synthesizing Vortioxetine according to the second aspect of the invention. This not only avoids the use of expensive palladium reagent and phosphine complex, but also reduces the steps of synthesizing Vortioxetine, and increases the yield significantly, thereby effectively reducing the cost of Vortioxetine.

In a third aspect, the invention also relates to the following intermediate compound of general formula II,

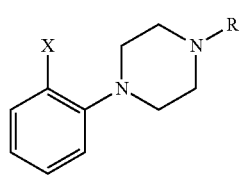

wherein, R is 9-fluorenylmethoxycarbonyl (Fmoc), carboxybenzyl (Cbz), acetyl (Ac) or trifluoroacetyl (Tfa), and preferably acetyl; X is halogen, selected from chlorine, bromine or iodine, and more preferably bromine. Moreover, the inventors found that compared to the compound of formula IIA disclosed in the prior art, these intermediates can further significantly shorten the subsequent reaction time during preparing Vortioxetine. In a last aspect, the invention relates to a method for synthesizing Vortioxetine represented by formula V, comprising: reacting the intermediate II according to the third aspect of the invention with compound III, wherein bis(2-diphenylphosphinophenyl)ether is used as phosphine ligand,

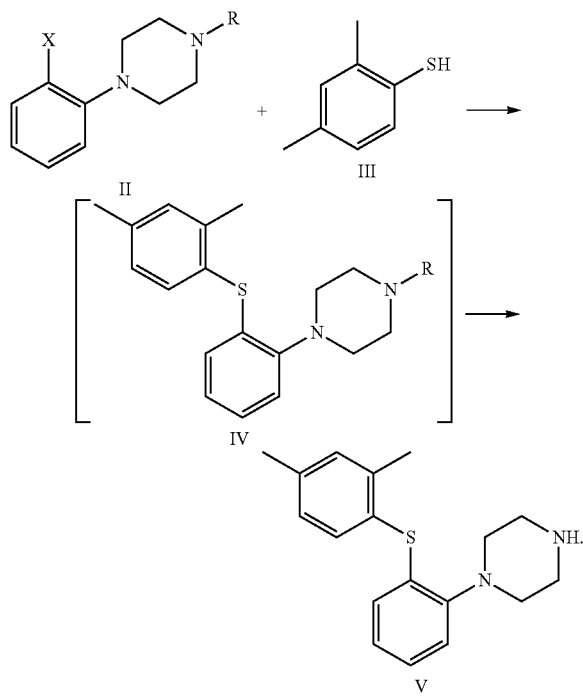

In a preferred embodiment, the obtained compound IV is hydrolyzed directly without being separated to obtain Vortioxetine represented by compound V.

In another preferred embodiment, the molar ratio of bis(2-diphenylphosphinophenyl)ether to intermediate II is 0.3 to 6.0%, preferably 0.75 to 1.5%, and more preferably 0.75 to 0.9%. The inventors found that the yield of Vortioxetine can be increased in a molar ratio of 0.75 to 1.5%, in particular 0.75 to 0.9% of bis(2-diphenylphosphinophenyl) ether to intermediate II. The reason for this is that the activity of palladium catalyst is increased, while the amount of palladium catalyst used is decreased. In the subsequent purification process, the operation related to removing palladium can be simplified to increase the yield.

The inventors unexpectedly found that the use of bis(2-diphenylphosphinophenyl)ether as phosphine ligand can effectively facilitate reaction. In addition, compared with other phosphine ligand, bis(2-diphenylphosphinophenyl) ether is much cheaper, thereby further decreasing the cost.

DETAILED DESCRIPTION OF THE INVENTION

EXAMPLE 1

EXAMPLE 1-1

Preparation of Compound I:
4-tert-butoxycarbonyl-1-(2-aminophenyl)piperazine

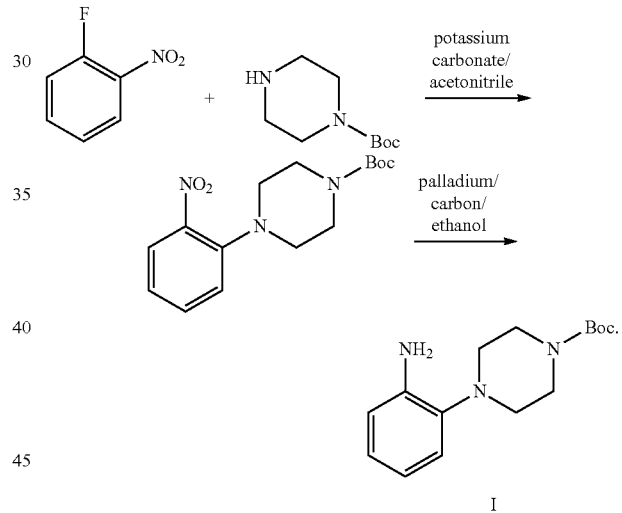

Ortho-fluoronitrobenzene (14.1 g, 0.1 mol), 4-tert-butoxycarbonyl-1-piperazine (18.6 g, 0.1 mol), and potassium carbonate (13.8 g, 0.4 mol) were added to acetonitrile (140 ml), stirred and heated to reflux. After reacting for 16 h, the reaction system was cooled to room temperature, filtered under reduced pressure to remove inorganic salts. Then, the filter cake was washed with acetonitrile (40 ml), and the filtrate was merged and concentrated to a slurry system under reduced pressure. Ethanol (140 ml) was added and concentrated to obtain a slurry system, after that ethanol (140 ml) was added, and stirred until clarification. Then a wet palladium/carbon (7% palladium) (1.12 g) was added. The system was purged with nitrogen gas (40 psi) for three times and then hydrogen gas (40 psi) for three times. Hydrogenation was carried out, under the pressure of 30 to 40 psi and at the temperature of 35 to 40° C. for 10 h, then cooled to room temperature, and filtered to remove palladium/carbon. The filter cake was washed with ethanol (30 ml), and the filtrate was merged and concentrated to dry under reduced pressure. A pale yellow solid of 25.3 g was obtained, and the yield was 91.2%; MS$^+$=278.2.

EXAMPLE 1-2

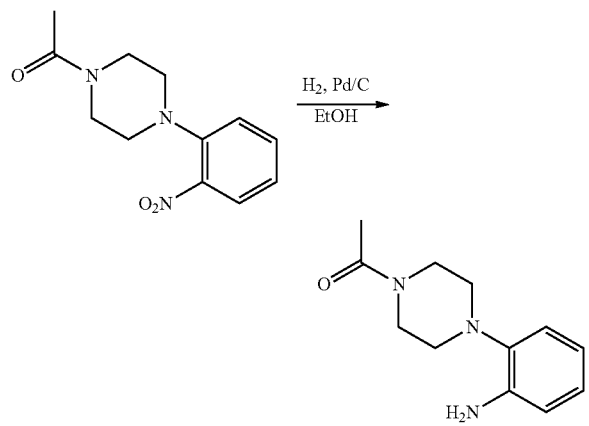

2-acetyl-piperazinylnitrobenzene (24.9 g, 0.1 mol) was added to ethanol (250 ml), and stirred until clarification. A wet palladium/carbon (1.12 g) was added, and hydrogenated (35 to 40° C., 40 psi) for 3 h. The reaction system was cooled to room temperature, and filtered to remove palladium/carbon. The filter cake was washed with ethanol (30 ml), and the filtrate was merged, and concentrated to dry under reduced pressure. Then, a pale yellow solid of 22.0 g was obtained, and the yield was 100%; MS$^+$=220.3.

EXAMPLE 2

EXAMPLE 2-1: PREPARATION OF COMPOUND II:
4-tert-butoxycarbonyl-1-(2-bromophenyl)piperazine

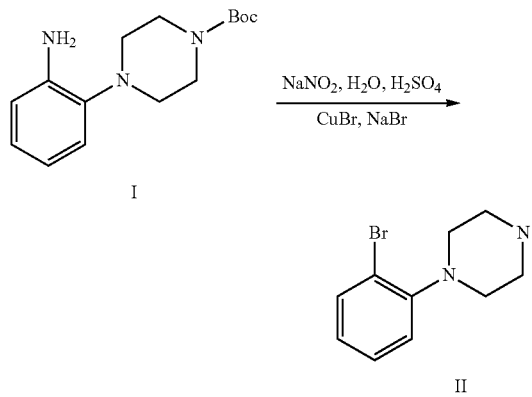

Concentrated sulfuric acid (98%) (7.6 g, 0.077 mol) was dropped slowly into water (180 ml), stirred, and cooled to 0 to 5° C. 4-tert-butoxycarbonyl-1-(2-aminophenyl)piperazine (20.0 g, 0.072 mol) was added slowly into the system and stirred. Sodium nitrite (5.2 g, 0.077 mol) was added into water (20 ml), stirred until clarification, and then slowly dropped into the raw material system while controlling the temperature to 0 to 10° C. After the completion of dropping, the reaction system was raised to room temperature, and stirred for half an hour to form a diazonium salt system. Sodium bromide (41.6 g, 0.288 mol) and cuprous bromide (10.4 g, 0.072 mol) were added into water (80 ml), stirred mechanically, and heated to an internal temperature of about 80° C. Then the aforementioned obtained diazonium salt system was dropped slowly into the system. After the completion of dropping, the reaction was performed for 3 h while maintaining the temperature. Then heating was stopped, and the reaction system was cooled to room temperature. Ethyl acetate (200 ml) was added, stirred for half an hour, and filtered under reduced pressure. The filter cake was washed with ethyl acetate (50 ml). The obtained dark green filtrate was layered. Aqueous phase was extracted with ethyl acetate (200 ml) once. Organic phases were merged, dried with anhydrous sodium sulfate (10.0 g, 0.07 mol), and then filtered under reduced pressure to remove the solids. The filtrates were merged, and distilled to remove acetyl acetate. The residue was distilled under reduced pressure (2 mm Hg), and the distillate in the range of 70 to 80° C. was collected to obtain a pale yellow oil of 18.42 g. The yield was 74.9%; MS$^+$=341.1.

EXAMPLES 2-2 to 2-19

Referring to example 2-1, the substituent groups R and X as well as halogenating agent are changed, and the results of the yields are shown in table 1.

TABLE 1

| Example | R group | X group | Halogenating agent | Yield (%) |
| --- | --- | --- | --- | --- |
| 2-2 | Cbz | Br | CuBr and NaBr | 60.3 |
| 2-3 | Ac | Br | CuBr and LiBr | 75.8 |
| 2-4 | Tfa | Br | CuBr and LiBr | 70.5 |
| 2-5 | Fmoc | Br | CuBr and LiBr | 66.8 |
| 2-6 | Ac | Br | NaBr | 62.6 |
| 2-7 | Ac | Br | KBr | 60.7 |
| 2-8 | Ac | Br | LiBr | 61.9 |
| 2-9 | Ac | Br | MgBr$_2$ | 60.0 |
| 2-10 | Ac | Br | CuBr | 58.6 |
| 2-11 | Ac | Br | CuBr and NaBr | 60.8 |
| 2-12 | Ac | Br | CuSO$_4$ and NaBr | 61.1 |
| 2-13 | Boc | Br | CuBr and LiBr | 69.5 |
| 2-14 | Ac | Br | CuBr$_2$ and LiBr | 62.8 |
| 2-15 | Ac | Cl | CuCl and KCl | 62.2 |
| 2-16 | Ac | I | CuI and KI | 62.0 |
| 2-17 | Ac | Cl | CuBr and NaBr | 75.2 |
| 2-18 | Ac | I | CuBr and NaBr | 74.3 |
| 2-19 | Ac | Br | CuBr and LiBr | 75.3 |

From the examples above, it can be seen that, compared with the method for synthesizing the intermediate IIA reported in the PCT Publication WO2004067703, the method for preparing the intermediate II of Vortioxetine provided by the invention not only has a higher yield, but also avoids the use of expensive and specific palladium reagent and phosphine complex, thereby effectively reducing the cost, and being suitable for industrial production. Moreover, the method for preparing the intermediate II of Vortioxetine provided by the invention avoids the use of expensive and specific palladium reagent and phosphine complex, thus it avoids the extreme process conditions related to the use of palladium reagent and phosphine complex, and is process-friendly.

EXAMPLE 3

EXAMPLE 3-1

Preparation of Compound V: Vortioxetine Hydrobromide

EXAMPLE 3-2

Preparation of Compound V: Vortioxetine Hydrobromide

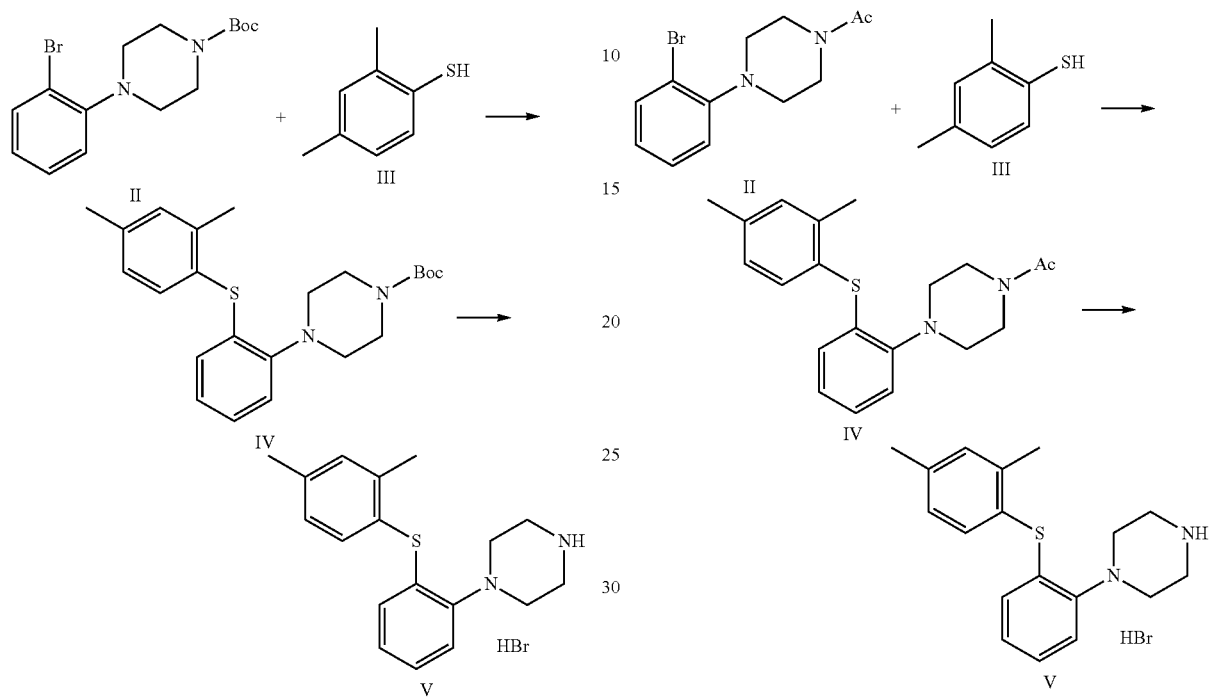

4-tert-butoxycarbonyl-1-(2-bromophenyl)piperazine (24.6 g, 0.07 mol), 2,4-dimethyl-thiophenol (10.0 g, 0.07 mol), sodium tert-butoxide (10.0 g, 0.1 mol), tri(dibenzalacetone)dipalladium ($Pd_2(dba)_3$) (0.78 g, 0.8 mmol) and 1,1'-binaphthyl-2,2'-bis(diphenylphosphine) (BINAP) (2.2 g, 3.5 mmol) were added into toluene (150 ml), and stirred. It was purged with nitrogen gas for three times and then protected with nitrogen gas. The system was heated to reflux, reacted for 24 h, cooled to room temperature, and filtered to remove insoluble substance. The filter cake was washed with toluene (30 ml), and the filtrate was merged and concentrated to dry under reduced pressure to obtain claret-red oil. The cold (0 to 10° C.) ethyl acetate (100 ml) was dropped slowly and a large amount of orange-yellow solid was precipitated. The system was stirred for 2 h while maintaining the temperature, and filtered under reduced pressure. The filter cake was washed with cold ethyl acetate (20 ml) to obtain orange solid, and dried to obtain compound IV. Compound IV was added into methanol (150 ml), and stirred until clarification. 48% hydrobromic acid (20 ml) was dropped slowly, and earthy yellow solid was separated out gradually from the system. The system was heated to reflux and reacted for 2 h, then cooled to 0 to 15° C., and stirred for 16 h. The system was concentrated to about 30 ml under reduced pressure. 200 ml ethyl acetate was added, and concentrated to get a slurry. A large amount of yellow solid was separated out from the system. Methyl tert-butyl ether (100 ml) was added, stirred for half an hour at room temperature and filtered. The filter cake was washed with methyl tert-butyl ether (30 ml) to obtain yellow solid of 18.2 g. The yield was 66.2%. $MS^+=299.2$.

4-acetyl-1-(2-bromophenyl)piperazine (19.8 g, 0.07 mol) prepared in example 2-3, 2,4-dimethyl-thiophenol (10.0 g, 0.07 mol), sodium tert-butoxide (10.0 g, 0.1 mol), tri(dibenzalacetone)dipalladium ($Pd_2(dba)_3$) (0.78 g, 0.8 mmol) and 1,1'-binaphthyl-2,2'-bis(diphenylphosphine) (BINAP) (2.2 g, 3.5 mmol) were added into toluene (150 ml), and stirred. It was purged with nitrogen gas for three times and protected with nitrogen gas. The system was heated to reflux and reacted for 10 h, then cooled to room temperature, and filtered to remove insoluble substance. The filter cake was washed with toluene (30 ml), and the filtrate was merged, and concentrated to dry under reduced pressure to obtain claret-red oil. The cold (0 to 10° C.) ethyl acetate (100 ml) was dropped slowly, and a large amount of orange-yellow solid was separated out. The system was stirred for 2 h while maintaining the temperature, and then filtered under reduced pressure. The filter cake was washed with cold ethyl acetate (20 ml) to obtain orange-yellow solid, and dried to obtain compound IV. Compound IV was added into methanol (150 ml), and stirred until clarification. 48% hydrobromic acid (20 ml) was dropped slowly, and earthy yellow solids were separated out gradually from the system. The system was heated to reflux and reacted for 2 h, then cooled to 0-15° C., and stirred for 5 h. The system was concentrated to about 30 ml under reduced pressure. 200 ml ethyl acetate was added, and concentrated to get a slurry. A large amount of yellow solid was separated out from the system. Methyl tert-butyl ether (100 ml) was added, stirred for half an hour at room temperature, and filtered. The filter cake was washed with methyl tert-butyl ether (30 ml) to obtain yellow solid of 18.2 g. The yield was 67.2%. $MS^+=299.2$.

EXAMPLE 3-3

Preparation of Compound V: Vortioxetine Hydrobromide

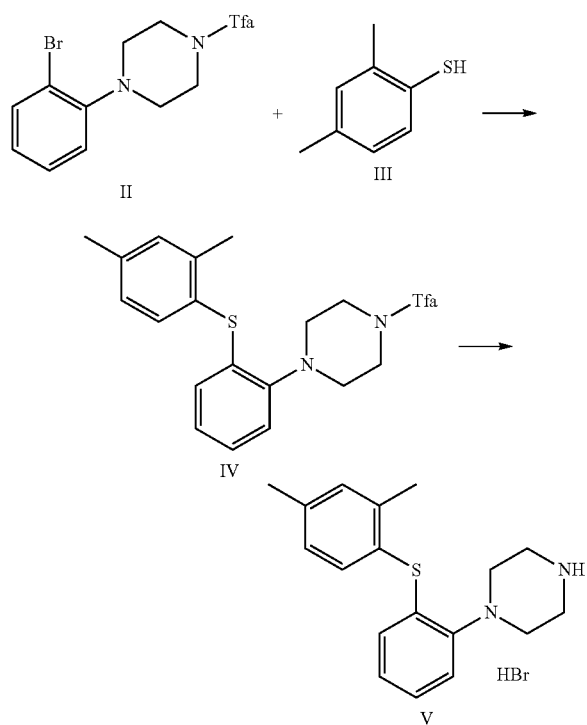

Vortioxetine hydrobromide was prepared in the same manner as that in example 3-2, except that 4-trifluoroacetyl-1-(2-bromophenyl)piperazine prepared in example 2-4 was used instead of 4-acetyl-1-(2-bromophenyl)piperazine. The yield was 66.9%.

EXAMPLE 3-4

Preparation of Compound V: Vortioxetine Hydrobromide

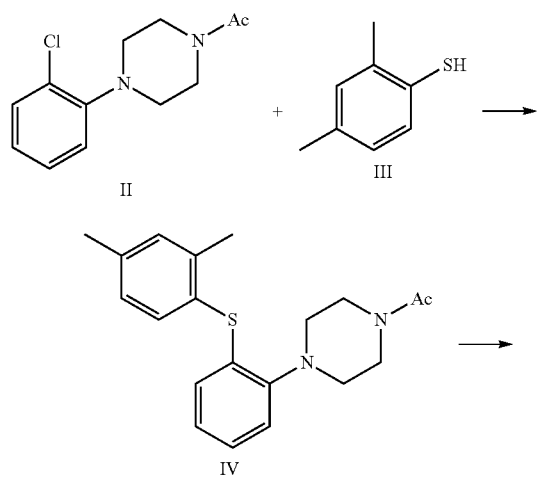

-continued

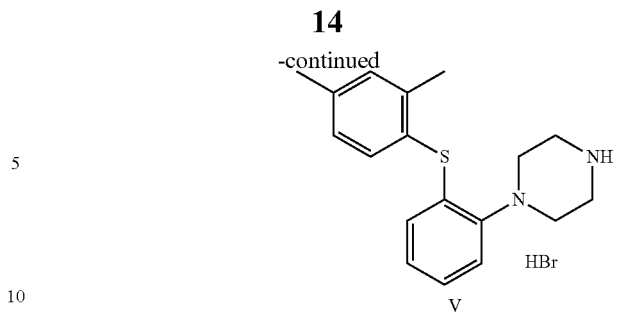

Vortioxetine hydrobromide was prepared in the same manner as that in example 3-2, except that 4-acetyl-1-(2-chlorophenyl)piperazine prepared in example 2-17 was used instead of 4-acetyl-1-(2-bromophenyl)piperazine. The yield was 67.8%.

EXAMPLE 3-5

Preparation of Compound V: Vortioxetine Hydrobromide

Vortioxetine hydrobromide was prepared in the same manner as that in example 3-2, except that 4-acetyl-1-(2-iodophenyl)piperazine prepared in example 2-18 was used instead of 4-acetyl-1-(2-bromophenyl)piperazine. The yield was 66.8%.

EXAMPLE 3-6

Preparation of Compound V: Vortioxetine Hydrobromide

Vortioxetine hydrobromide was prepared in the same manner as that in example 3-2, except that 4-carboxybenzyl-1-(2-bromophenyl)piperazine prepared in example 2-2 was used instead of 4-acetyl-1-(2-bromophenyl)piperazine. The yield was 66.4%.

EXAMPLE 3-7

Preparation of Compound V: Vortioxetine Hydrobromide

Vortioxetine hydrobromide was prepared in the same manner as that in example 3-2, except that 4-(9-fluorenyl-methoxycarbonyl)-1-(2-bromophenyl)piperazine prepared in example 2-5 was used instead of 4-acetyl-1-(2-bromophenyl)piperazine. The yield was 66.1%.

EXAMPLE 4

EXAMPLE 4-1

Preparation of Compound V: Vortioxetine Hydrobromide

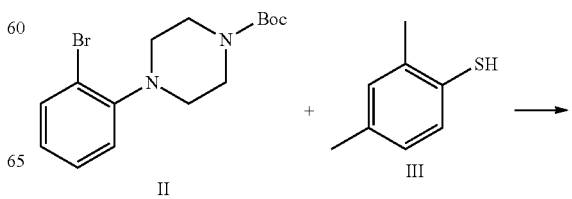

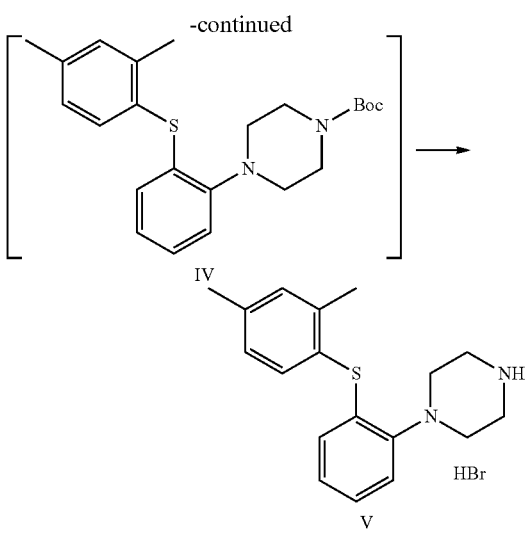

4-tert-butoxycarbonyl-1-(2-bromophenyl)piperazine (24.6 g, 0.07 mol), 2,4-dimethyl-thiophenol (10.0 g, 0.07 mol), sodium tert-butoxide (10.0 g, 0.1 mol), tri(dibenzalacetone)dipalladium ($Pd_2(dba)_3$) (0.78 g, 0.8 mmol) and 1,1'-binaphthyl-2,2'-bis(diphenylphosphine) (BINAP) (2.2 g, 3.5 mmol) were added into toluene (150 ml), and stirred. It was purged with nitrogen gas for three times and then protected with nitrogen gas. The system was heated to reflux and reacted for 24 h, then cooled to room temperature, and filtered to remove insoluble substance. The filter cake was washed with toluene (30 ml), and the filtrate was merged, and concentrated to dry under reduced pressure to obtain claret-red oil. Methanol (150 ml) was added, and stirred to clarification. 48% hydrobromic acid (20 ml) was dropped slowly, and earthy yellow solids were precipitated gradually from the system. The system was heated to reflux and reacted for 2 h, then cooled to 0 to 15° C., and stirred for 16 h. The system was concentrated to about 30 ml under reduced pressure. 200 ml ethyl acetate was added, and concentrated to get a slurry. A large amount of yellow solid was separated out from the system. Methyl tert-butyl ether (100 ml) was added, and stirred for half an hour at room temperature. The system was filtered, and the filter cake was washed with methyl tert-butyl ether (30 ml) to obtain yellow solid of 20.6 g. The yield was 75.3%.

EXAMPLE 4-2

4-acetyl-1-(2-bromophenyl)piperazine (19.8 g, 0.07 mol) prepared in example 2-3, 2,4-dimethyl-thiophenol (10.0 g, 0.07 mol), sodium tert-butoxide (10.0 g, 0.1 mol), tri(dibenzalacetone)dipalladium ($Pd_2(dba)_3$) (0.78 g, 0.8 mmol) and 1,1'-binaphthyl-2,2'-bis(diphenylphosphine) (BINAP) (2.2 g, 3.5 mmol) were added into toluene (150 ml), and stirred. It was purged with nitrogen gas for three times and then protected with nitrogen gas. The system was heated to reflux and reacted for 10 h, then cooled to room temperature, and filtered to remove insoluble substance. The filter cake was washed with toluene (30 ml), and the filtrate was merged, and concentrated to dry under reduced pressure to obtain claret-red oil. Methanol (150 ml) was added, and stirred to clarification. 48% hydrobromic acid (20 ml) was dropped slowly, and earthy yellow solids were percitated gradually from the system. The system was heated to reflux and reacted for 2 h, then cooled to 0 to 15° C., and stirred for 5 h. The system was concentrated to about 30 ml under reduced pressure, and 200 ml ethyl acetate was added and concentrated to get a slurry. A large amount of yellow solid was separated out from the system. Methyl tert-butyl ether (100 ml) was added, and stirred for half an hour at room temperature. The system was filtered, and the filter cake was washed with methyl tert-butyl ether (30 ml) to obtain yellow solids of 20.6 g. The yield was 78.3%.

EXAMPLE 4-3

Vortioxetine hydrobromide was prepared in the same manner as that in example 4-2, except that 4-trifluoroacetyl-1-(2-bromophenyl)piperazine prepared in example 2-4 was used instead of 4-acetyl-1-(2-bromophenyl)piperazine. The yield was 76.9%.

EXAMPLE 4-4

Vortioxetine hydrobromide was prepared in the same manner as that in example 4-2, except that 4-acetyl-1-(2-chlorophenyl)piperazine prepared in example 2-17 was used instead of 4-acetyl-1-(2-bromophenyl)piperazine. The yield was 77.8%.

EXAMPLE 4-5

Vortioxetine hydrobromide was prepared in the same manner as that in example 4-2, except that 4-acetyl-1-(2-iodophenyl)piperazine prepared in example 2-18 was used instead of 4-acetyl-1-(2-bromophenyl)piperazine. The yield was 76.8%.

EXAMPLE 4-6

Preparation of Compound V: Vortioxetine Hydrobromide

Vortioxetine hydrobromide was prepared in the same manner as that in example 4-2, except that 4-carboxybenzyl-1-(2-bromophenyl)piperazine prepared in example 2-2 was used instead of 4-acetyl-1-(2-bromophenyl)piperazine. The yield was 76.4%.

EXAMPLE 4-7

Preparation of Compound V: Vortioxetine Hydrobromide

Vortioxetine hydrobromide was prepared in the same manner as that in example 4-2, except that 4-(9-fluorenyl-methoxycarbonyl)-1-(2-bromophenyl)piperazine prepared in example 2-5 was used instead of 4-acetyl-1-(2-bromophenyl)piperazine. The yield was 76.1%.

EXAMPLE 5

EXAMPLE 5-1

Preparation of Compound V: Vortioxetine Hydrobromide

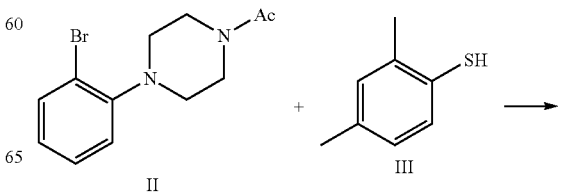

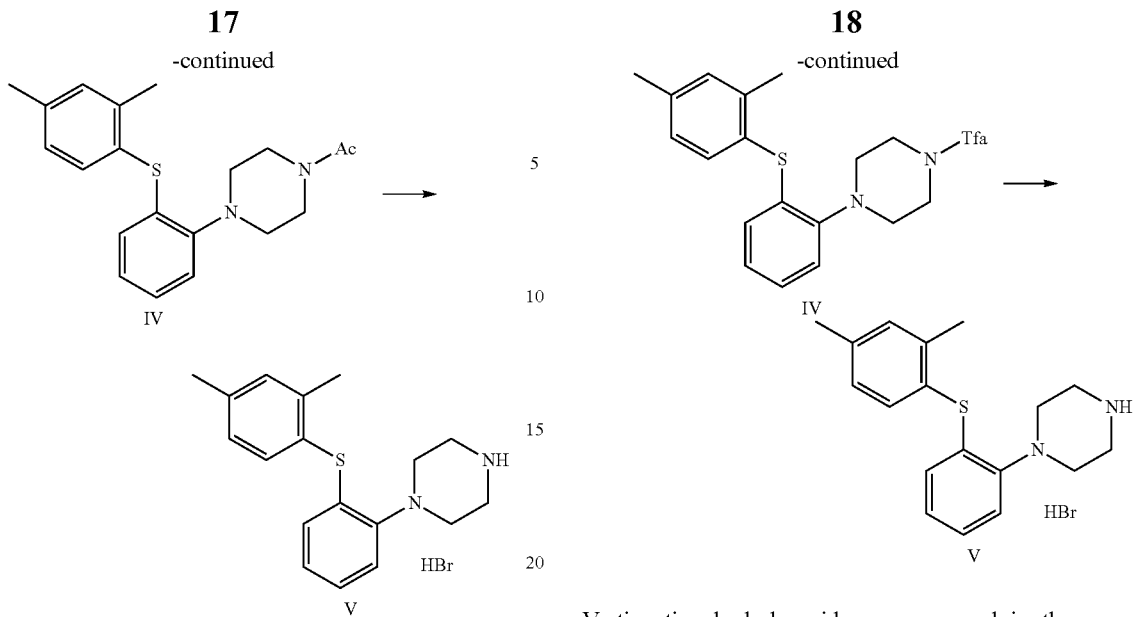

4-acetyl-1-(2-bromophenyl)piperazine (30.0 g, 0.106 mol) prepared in example 2-3, 2,4-dimethyl-thiophenol (14.7 g, 0.106 mol), potassium tert-butoxide (35.67 g, 0.318 mol), tri(dibenzalacetone)dipalladium ($Pd_2(dba)_3$) (0.243 g, 0.27 mmol) and bis(2-diphenylphosphino phenyl)ether (DPEphos) (0.428 g, 0.8 mmol) were added into toluene (300 ml), and stirred. It was purged with nitrogen gas for three times and then protected with nitrogen gas. The system was heated to reflux and reacted for 10 h, and cooled to room temperature. 150 ml water was added, stirred for 30 min, and filtered to remove insoluble substance. The filter cake was washed with toluene (30 ml), and the filtrate was merged. Toluene layer was separated, and toluene phase was concentrated to dry under reduced pressure to obtain claret-red oil. Methanol (120 ml) and an aqueous solution (60 ml) of KOH (29.7 g, 0.53 mol) were added. The system was heated to reflux and reacted for 24 h. The system was concentrated to about 90 ml under reduced pressure, and 300 ml toluene and 90 ml water were added. Toluene phase was separated. 26.8 g (0.159 mol) of 48% hydrobromic acid was dropped into the toluene phase. A large amount of solid was separated out. The system was stirred for 2 h at 0 to 20° C., and filtered. The filter cake was washed with 15 ml toluene once to obtain yellow solid of 35.1 g. The yield was 87.4%.

EXAMPLE 5-2

Preparation of Compound V: Vortioxetine Hydrobromide

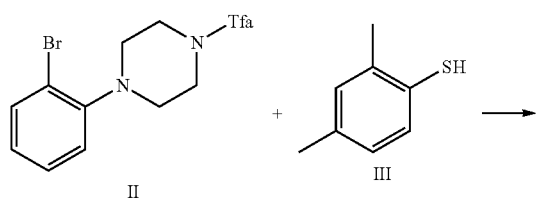

Vortioxetine hydrobromide was prepared in the same manner as that in example 5-1, except that 4-trifluoroacetyl-1-(2-bromophenyl)piperazine prepared in example 2-4 was used instead of 4-acetyl-1-(2-bromophenyl)piperazine. The yield was 85.2%.

EXAMPLE 5-3

Preparation of Compound V: Vortioxetine Hydrobromide

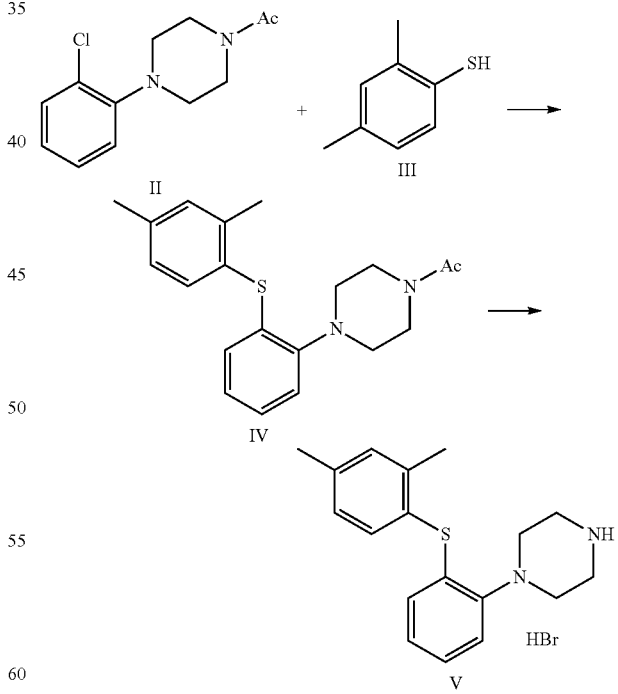

Vortioxetine hydrobromide was prepared in the same manner as that in example 5-1, except that 4-acetyl-1-(2-chlorophenyl)piperazine prepared in example 2-17 was used instead of 4-acetyl-1-(2-bromophenyl)piperazine. The yield was 67.4%.

EXAMPLE 5-4

Preparation of Compound V: Vortioxetine Hydrobromide

Vortioxetine hydrobromide was prepared in the same manner as that in example 5-1, except that 4-acetyl-1-(2-iodophenyl)piperazine prepared in example 2-18 was used instead of 4-acetyl-1-(2-bromophenyl)piperazine. The yield is 81.7%.

EXAMPLE 5-5

Preparation of Compound V: Vortioxetine Hydrobromide

Vortioxetine hydrobromide was prepared in the same manner as that in example 5-1, except that 4-carboxybenzyl-1-(2-bromophenyl)piperazine prepared in example 2-2 was used instead of 4-acetyl-1-(2-bromophenyl)piperazine. The yield is 77.6%.

EXAMPLE 5-6

Preparation of Compound V: Vortioxetine Hydrobromide

Vortioxetine hydrobromide was prepared in the same manner as that in example 5-1, except that 4-(9-fluorenylmethoxycarbonyl)-1-(2-bromophenyl)piperazine prepared in example 2-5 was used instead of 4-acetyl-1-(2-bromophenyl)piperazine. The yield is 80.5%.

The description of examples above is only used for helping to understand the processes and core concepts of the invention. It is pointed out that for the person having ordinary skill in the art, various improvements and modifications can be also made in the present invention without departing from the principle of the present invention, and these improvements and modifications are fallen into the protection scope of the claims of the present invention.

What is claimed is:

1. A method for synthesizing an intermediate II, characterized by firstly diazotizing a compound of formula I as a raw material, and then halogenating to obtain the intermediate II:

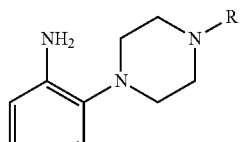

I

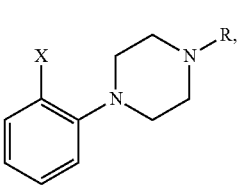

II in each formula, R is a protective group for amino, and X is halogen.

2. The method of claim 1, wherein R is selected from: tert-butoxycarbonyl, 9-fluorenylmethoxycarbonyl, carboxybenzyl, acetyl or trifluoroacetyl.

3. The method of claim 2, wherein R is tert-butoxycarbonyl or acetyl.

4. The method of claim 1, wherein X is selected from: chlorine, bromine or iodine.

5. The method of claim 4, wherein X is bromine.

6. The method of claim 1, wherein the halogenating agent used in the halogenating reaction is selected from: NaX, KX, LiX, $MgX_2$, CuX, $CuX_2$, or a mixture of any two thereof, or a mixture of copper sulfate and NaX.

7. The method of claim 6, wherein the halogenating agent is a mixture of sodium bromide and cuprous bromide, or a mixture of lithium bromide and cuprous bromide.

8. The method of claim 1, further comprising reacting the intermediate II with a compound III to obtain a compound IV, hydrolyzing the obtained compound IV directly without being separated to obtain Vortioxetine represented by compound V,

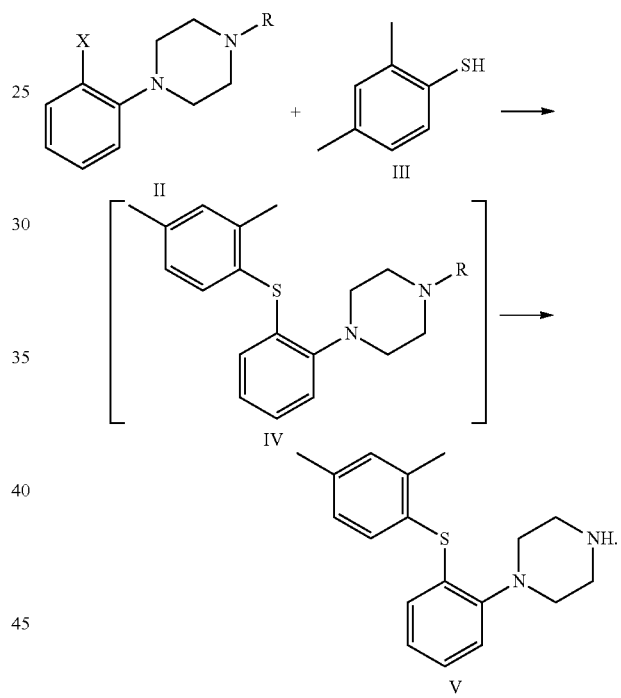

9. A compound of following formula

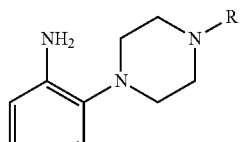

II

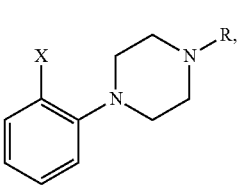

wherein R is 9-fluorenylmethoxycarbonyl or carboxybenzyl; and X is halogen.

10. The compound of claim 9, wherein X is selected from: chlorine, bromine or iodine.

11. The compound of claim 10, wherein X is bromine.

12. A method for synthesizing Vortioxetine represented by formula V, comprising: reacting the intermediate II with the compound III, wherein bis(2-diphenylphosphinophenyl) ether is used as a phosphine ligand,

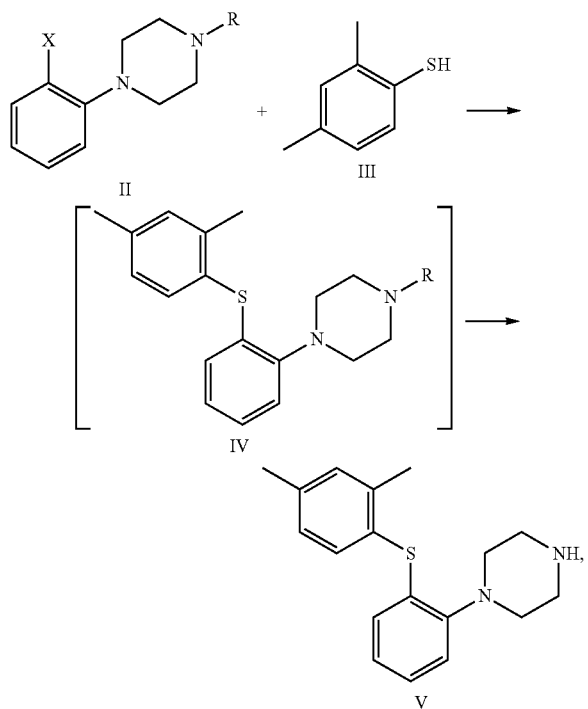

wherein R is acetyl, 9-fluorenylmethoxycarbonyl, carboxybenzyl, or truflyoroacetyl; and X is a halogen.

13. The method of claim 12, wherein the obtained compound IV is hydrolyzed directly without being separated to obtain Vortioxetine represented by compound V.

14. The method of claim 12, wherein the molar ratio of bis(2-diphenylphosphinophenyl)ether to the intermediate II is 0.6 to 6.0%.

15. The method of claim 13, wherein the molar ratio of bis(2-diphenylphosphinophenyl)ether to the intermediate II is 0.6 to 6.0%.

16. The method of claim 12, wherein the molar ratio of bis(2-diphenylphosphinophenyl)ether to the intermediate II is 0.75 to 1.5%.

17. The method of claim 12, wherein the molar ratio of bis(2-diphenylphosphinophenyl)ether to the intermediate II is 0.75 to 0.9%.

18. The method of claim 13, wherein the molar ratio of bis(2-diphenylphosphinophenyl)ether to the intermediate II is 0.75 to 1.5%.

19. The method of claim 13, wherein the molar ratio of bis(2-diphenylphosphinophenyl)ether to the intermediate II is 0.75 to 0.9%.

* * * * *